(12) United States Patent
Blackner

(10) Patent No.: US 10,143,679 B2
(45) Date of Patent: Dec. 4, 2018

(54) PHYTOESTROGEN COMPOSITIONS AND ASSOCIATED METHODS

(71) Applicant: NSE Products, Inc., Provo, UT (US)

(72) Inventor: Lori Blackner, South Jordan, UT (US)

(73) Assignee: NSE Products, Inc., Provo, UT (US)

( * ) Notice: Subject to any disclaimer, the term of this patent is extended or adjusted under 35 U.S.C. 154(b) by 0 days.

(21) Appl. No.: 15/721,424

(22) Filed: Sep. 29, 2017

(65) Prior Publication Data

US 2018/0271834 A1 Sep. 27, 2018

Related U.S. Application Data

(63) Continuation of application No. 14/278,216, filed on May 15, 2014, which is a continuation of application No. 12/191,378, filed on Aug. 14, 2008, which is a continuation of application No. 11/334,768, filed on Jan. 17, 2006, which is a continuation of application No. 11/255,169, filed on Oct. 19, 2005.

(60) Provisional application No. 60/622,344, filed on Oct. 25, 2004.

(51) Int. Cl.
| | | |
|---|---|---|
| *A61K 31/56* | (2006.01) | |
| *A61K 31/404* | (2006.01) | |
| *A61K 31/353* | (2006.01) | |
| *A61K 31/352* | (2006.01) | |

(52) U.S. Cl.
CPC .......... *A61K 31/404* (2013.01); *A61K 31/352* (2013.01); *A61K 31/353* (2013.01)

(58) Field of Classification Search
CPC .................................................. A61K 31/56
See application file for complete search history.

(56) References Cited

U.S. PATENT DOCUMENTS

| | | | |
|---|---|---|---|
| 5,516,528 | A | 5/1996 | Hughes et al. |
| 5,942,539 | A | 8/1999 | Hughes, Jr. et al. |
| 6,086,915 | A | 7/2000 | Zeligs et al. |
| 6,497,906 | B1 | 12/2002 | Kelly |
| 6,518,319 | B1 | 2/2003 | Empie et al. |
| 6,583,129 | B1 | 6/2003 | Mazer et al. |
| 6,605,605 | B2 | 8/2003 | Hammerly |
| 6,613,792 | B1 | 9/2003 | Ellenberger et al. |
| 6,689,387 | B1 | 2/2004 | Zeligs |
| 2001/0031744 | A1 | 10/2001 | Kosbab |
| 2002/0058648 | A1 | 5/2002 | Hammerly |
| 2002/0192310 | A1 | 12/2002 | Bland et al. |
| 2003/0190381 | A1 | 10/2003 | Bland et al. |

FOREIGN PATENT DOCUMENTS

WO   WO 01/08637 A2   2/2001

OTHER PUBLICATIONS

Lu et al. Cancer Research, 2000;60:1299-1305.*
Atkinson et al.; "Urinary equol excretion in relation to 2-hydroxyestrone and 16alpha-hydroxyestrone concentrations: an observational study young to middle-aged women"; J Steroid Biochem Mol Biol; (Jul. 2003); p. 71-77; vol. 86(1); National Library of Medicine; (abstract) < PMID: 12943746 > [PubMed—indexed for MEDLINE].
Auborn et al.; "Indole-3-Carbinol Is a Negative Regulator of Estrogen"; Nutritional Genomics in Cancer Processes; (2003); pp. 2470S-2475S; vol. 133, No. 7 supplement; in: The Journal of Nutrition, [presented at the Nutritional Genomics and Proteomics in Cancer Prevention Conference (Sep. 5-6, 2002) Bethesda, MD; (2003); American Society for Nutritional Sciences.
Brooks et al.; "Supplementation with flaxseed alters estrogen metabolism in postmenopausal women to a greater extent than does supplementation with an equal amount of soy"; American Journal of Clinical Nutrition; (2004); p. 318-325; vol. 79(2); American Society for Clinical Nutrition.
Cauley et al.; "Estrogen metabolites and the risk of breast cancer in older women"; Epidemiology; (Nov. 2003); p. 740-744; vol. 14(6); National Library of Medicine; (abstract) < PMID: 14569192 > [PubMed—indexed for MEDLINE].
Haggans et al.; "The effect of flaxseed and wheat bran consumption on urinary estrogen metabolites in premenopausal women"; Cancer Epidemiology, Biomarkers & Prevention; (Jul. 2000); p. 719-725; vol. 9 (7); National Library of Medicine.
Hutchins et al.; "Flaxseed influences urinary lignan excretion in a dose-dependent manner in post menopausal women"; Cancer Epidemiology, Biomarkers & Prevention; (Oct. 2000); p. 1113-1118; vol. 9(10); National Library of Medicine; (abstract) < PMID: 11045796 > [PubMed—indexed for Medline].
Jellinck et al.; "Ah Receptor Binding Properties of Indole Carbinols and Induction of Hepatic Estradiol Hydroxylation"; Biochemical Pharmocology; (1993); p. 1129-1136; vol. 45(5).
Kishida et al.; "Effect of dietary soy isoflavone aglycones on the urinary 16alpha-2-hydroxyestrone ratio in C3H/HeJ mice"; Nutr Cancer; (2000); p. 209-214; vol. 38(2); National Library of Medicine; (abstract) < PMID: 11525599 > [PubMed—indexed for Medline].
Kishida et al.; "Soy isoflavonoid aglycons genistein and daidzein Do not increase cytochrome P-450 content of the liver microsomes of mice"; J. Agric Food Chem; (Sep. 2000); p. 3872-3875; vol. 48(9); National Library of Medicine; (abstract) < PMID: 10995284 > [PubMed—indexed for Medline].
Kurzer; "Hormonal effects of soy in premenopausal women and men"; J. Nutr; (Mar. 2002); p. 570S-573S; vol. 132(3); National Library of Medicine; (abstract) < PMID: 11880595 > [PubMed—indexed for Medline].
Lian et al.; "Modulation of the constitutive activated STAT3 transcription factor in pancreatic cancer prevention: effects of indole-3-carbinol (I3C) and genistein"; Anticancer Res.; (Jan.-Feb. 2004); p. 133-137; vol. 24(1); National Library of Medicine; (abstract) < PMID: 15015587 > [PubMed—indexed for Medline].
Linumlife Science; Scientific evidence for women's health applications; Acatris; 9 pages; www.acatris.com.

(Continued)

*Primary Examiner* — San Ming R Hui
(74) *Attorney, Agent, or Firm* — Thorpe North & Western, LLP; David W. Osborne

(57) ABSTRACT

Methods for controlling estrogen metabolite formation in a subject and compositions for use therein are disclosed and described. In one aspect, estrogen metabolite formation may be controlled by coadministering an effective amount of a phytoestrogen and an indole compound.

17 Claims, No Drawings

(56) References Cited

OTHER PUBLICATIONS

Linumlife; Dosage Overview: Men's Health; Acatris; 1 page; www.acatris.com.

Linumlife; Dosage Overview: Women's Health; Acatris; 1 page; www.acatris.com.

Linumlife; First Standardized Flax Lignan Extract; www.acatris.com; 4 pages.

Lu et al.; "Increased Urinary Excretion of 2-Hydroxyestrone but not 16α-Hydroxyestrone in Premenopausal Women during a Soya Diet Containing Isoflavones"; Cancer Research; (Mar. 2000); p. 1299-1305; vol. 60.

Sarkar et al.; "Bax Translocation to Mitochondria is an Important Event in Inducing Apoptotic Cell Dealth by Indole-3-Carbinol (I3C) Treatment of Breast Cancer Cells"; Nutritional Genomics in Cancer Processes; American Society for Nutritional Sciences; (2003); p. 2434S-2439S; vol. 133.

Thompson et al.; "Phytoestrogen Content of Foods Consumed in Canada, Including Isoflavones, Lignans, and Coumestan"; Nutrition and Cancer; (2006); pp. 184-201; vol. 54, No. 2.

Wang et al.; "Mammalian phytoestrogens: enterodiol and enterolactone"; Review; Journal of Chromatography B; (2002); p. 289-309; vol. 777; Elsevier.

Xu et al.; "Effects of soy isoflavones on estrogen and phytoestrogen metabolism in premenopausal women"; Cancer Epidemiology Biomarkers & Prevention; (Dec. 1998); p. 1101-1108; vol. 7(12); National Library of Medicine; (abstract) < PMID: 9865428 > [PubMed—indexed for Medline].

Xu et al.; "Soy consumption alters endogenous estrogen metabolism in postmenopausal women"; Cancer Epidemiology, Biomarkers & Prevention; (Aug. 2000); p. 781-786; vol. 9(8); National Library of Medicine; (abstract) < PMID: 10952094 > [PubMed—indexed for Medline].

\* cited by examiner

PHYTOESTROGEN COMPOSITIONS AND ASSOCIATED METHODS

This application is a continuation of U.S. patent application Ser. No. 14/278,216 filed on May 15, 2014, which is a continuation of U.S. patent application Ser. No. 12/191,378 filed on Aug. 14, 2008, which is a continuation of U.S. patent application Ser. No. 11/334,768, filed on Jan. 17, 2006, which is a continuation of U.S. patent application Ser. No. 11/255,169, filed on Oct. 19, 2005, which claims the benefit of U.S. Provisional Patent Application Ser. No. 60/622,344 filed on Oct. 25, 2004, each of which is incorporated herein by reference in their entirety.

THE FIELD OF THE INVENTION

This invention relates to compositions and methods for administration of phytoestrogens to women. Accordingly, the invention involves the fields of botany, nutritional and health sciences and medicine.

BACKGROUND OF THE INVENTION

Many women have a difficult time managing the effects of hormonal changes that accompany the aging body. Many women suffer from known hormonal conditions and symptoms as a result of hormonal imbalances or deficiencies, such as, menopause, endometriosis, osteoporosis, heart disease, cancer in particular breast cancer, hot flashes, night sweats, vaginal dryness, mood changes, and musculoskeletal symptoms. At present, hormonal imbalances and conditions are routinely treated with a variety of hormonal therapies.

In addition, a number of hormonal therapies have been used for purposes of contraception. In particular, compositions that utilize conjugated estrogens and/or a progesterone, such as those sold by Wyeth-Aerst under the name PREMARIN® and PREMPRO® are widely known and used.

It is now known that some estrogen therapies, despite their immediate benefits, may increase the long term incidences of certain life threatening conditions, such as cancer. It is thought that this is due, at least in part, to the abundance of active estrogen metabolites produced by the liver upon administration of traditional estrogens. For example, estradiol is the most biologically active and potent estrogen in the body. Estradiol is most often associated with the growth of breast and reproductive tissues and development of skeletal homeostasis. When estradiol is metabolized, it is first oxidized to estrone and then hydrolulated by 2-hydroxylase and 16-hydroxylase enzymes in the liver. This reaction produces the metabolites of 16-alphahydroxyestrone (active) and 2-hydroxyestrone (inactive).

Indole compounds, specifically indole-3-carbinol compounds are naturally occurring compounds derived from various plant sources, particularly, cruciferous plants such as broccoli, cabbage, turnips and brussel sprouts. Indole-3-carbinol is a member of the glucosinolates chemical group, a sulfur-containing chemical compound. Indole-3-carbinol compounds are antioxidants and have heretofore been primarily recognized as useful for cancer prevention. See, Auborn, Fan, Rosen, Goodwin, Chandraskaren, Williams, Chen and Carter, "Indole-3-Carbinol Is a Negative Regulator of Estrogen," American Society for Nutritional Sciences (2003). However, there has been some indication that administration of indole-3-carbinol can reduce the amount of active estrogen metabolites resulting from typical estrogen therapy, or from metabolism of endogenous estrogen.

Phytoestrogens are naturally occurring phenolic plant compounds which are found in many food and/or plant sources, such as, beans, cabbage, soybean, grains, and hops. Generally, phytoestrogens are extracted from seeds, stems, flowers and roots of plants and food sources. Phytoestrogens are structurally similar to estrogen and estradiol produced by mammals. For this reason, phytoestrogens can play an important roll in dietary supplementation for subjects suffering from a hormonal imbalance. However, most phytoestrogens are less potent than traditional estrogens and need to be consumed in large quantities in order to have a significant estrogenic effect. It is now also thought that administration of phytoestrogens may also increase production of 2-hydroxyestrone.

In view of the foregoing, compositions and methods which provide an estrogen supplementation benefit and reduce the in-vivo production of active estrogen metabolites continue to be sought.

SUMMARY OF THE INVENTION

Accordingly, the present invention provides methods of controlling estrogen metabolite formation. Generally speaking, one method involves coadministering to a subject, an effective amount of a phytoestrogen compound with an effective amount of an indole compound. It is thought that the coadministration of these two compounds provides a synergistic increase in the production of the inactive estrogen metabolite 2-hydroxyestrone as compared to the production of this metabolite attained by administration of either the phytoestrogen or the indole compound alone.

In one aspect, the present invention provides a method for synergistically biasing estrogen metabolism in a subject toward the production of the 2-hydroxyestrone metabolite. Such a method involves administering to a subject an effective amount of an indole compound and an effective amount of phytoestrogen. The combination of two compounds, such as, an indole compound and phytoestrogen compound, synergistically favors the estrogen metabolism to produce the inactive 2-hydroxyestrogen metabolite.

In yet another aspect of the present invention, an estrogen metabolite controlling composition is provided. The composition incorporates a synergistically effective amount of an indole compound and a phytoestrogen compound. Administering effective amounts of a composition according to the present invention can synergistically affect the estrogen metabolism. The composition is thought to produce a shift in the estrogen metabolism increasing the production of the more favorable 2-hydroxyestrone metabolite.

Examples of specific indole compounds that may be used in the present invention include but are not limited to: indole-3-carbinol, indoleacetic acid, indolebutyric acid, indolmycin, 3-indolylacetone, indomethacin, and indoramin. However, in one aspect, the indole compound may be an indole-3-carbinol.

Examples of specific phytoestrogen compounds that may be used in the present invention include but are not limited to plant derived compounds having a diphenolic structure resembling the structure of many potent synthetic estrogens, such as diethylstilbesterol and hexestrol. Specific examples of such compounds include without limitation various isoflavones such as genistein, diadzein, equol, and glycosides thereof and mixtures thereof. However, in one aspect, the phytoestrogen may be genistein. In one aspect of the present invention, the indole compound is indole-3-carbinol, and the phytoestrogen is genistein. Furthermore, the composition may include at least one excipient and/or at least one pharmaceutically acceptable carrier.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

Definitions

In describing and claiming the present invention, the following terminology will be used.

As used herein, "formulation" and "composition" may be used interchangeably herein, and refer to a combination of two or more elements, or substances. In some embodiments a composition may include an active agent and a carrier.

As used herein, "effective amount" refers to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, "carrier" or "inert carrier" refers to a substance with which a bioactive agent may be combined to achieve a specific dosage formulation for delivery to a subject. As a general principle, carriers must not react with the bioactive agent in a manner which substantially degrades or otherwise adversely affects the bioactive agent.

As used herein, "excipient" refers to substantially inert substance which may be combined with an active agent and a carrier to achieve a specific dosage formulation for delivery to a subject, or to provide a dosage form with specific performance properties. For example, excipients may include binders, lubricants, etc., but specifically exclude active agents and carriers.

As used herein, "subject" refers to a mammal that may benefit from the administration of a composition or method as recited herein. Most often, the subject will be a human.

As used herein, "administration," and "administering" refer to the manner in which an active agent, or composition containing such, is presented to a subject. Administration can be accomplished by various routes well-known in the art such as oral, and non-oral methods.

As used herein, "coadministration" refers to administration of two or more active agents in a manner that will allow them to be present together in-vivo for period of time. Accordingly, while the term "coadministration" includes simultaneous administration of two or more active agents, and administration from a single formulation, it is to be understood that it is not limited thereto.

"Oral administration" can be achieved by swallowing, chewing, or sucking of an oral dosage form comprising the drug. Examples of well known oral dosage forms include tablets, capsules, caplets, powders, granulates, beverages, syrups, elixirs, confections, or other food items, etc.

"Estrogen", and "estrogenic hormone" refer to any substance, natural or synthetic, that exerts a biological or pharmacological action primarily by binding to estrogen receptors. Examples include but are not limited to: 17-.beta.-estradiol, 17-.alpha.-estradiol, estradiol, estrone, and phytoestrogens. These estrogens may be derivatized or modified to form, for example, conjugated equine estrogens, esterified estrogens, ethinyl estradiol, etc. Examples of esterified estrogens include but are not limited to: estradiol-3,17-diacetate, estradiol-3-acetate, estradiol-17-acetate, estradiol-3,17-divalerate, estradiol-3-valerate, and estradiol-17-valerate. Also included are selective estrogen receptor modulators (SERMS), for example raloxifene, available under the tradename Evista.®. from Eli Lilly, and the like. The estrogens may also be present as salts, (e.g., as sodium estrogen sulfate), isomers, or prodrugs.

As used herein, "phytoestrogens" refers to compounds that provide an estrogenic effect when administered to a subject, which are derived from plants. One key characteristic of such compounds is a diphenolic structure that resembles the structure of potent synthetic estrogens such as diethylstilbesterol and hexestrol. Isoflavones are one major class of compounds exhibiting such structure. Typical isoflavones found in humans include, but are not limited to genistein, diadzein, and equol.

"Synergistic", "synergism", "synergistically effective" or "synergistically enhances", may be used interchangeably and refer to a situation in which the combined effect of two agents is greater than which would be predicted from their individual effects. Various mechanisms for calculating or otherwise determining synergism are known to those of ordinary skill in the art.

"Improving health" refers to reducing, improving, or preventing the incidence and/or intensity of symptoms associated with estrogen deficiency.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

The Invention

It is known that women experiencing menopausal symptoms or other estrogen deficiency symptoms may gain relief from administration of an estrogen supplement. Further, many women may have their health improved through estrogen supplementation. Examples of conditions that are known to be responsive to, ameliorated by, or prevented by estrogen supplementation include, menopause discomfort, endometriosis, osteoporosis, heart disease, cancer, in particular breast cancer, hot flashes, cramps, night sweats, vaginal dryness, mood changes, and musculoskeletal symptoms, and combinations thereof. Further still, estrogens are widely used as oral contraceptives.

In one aspect the present invention provides methods and compositions for controlling estrogen metabolite formation in a subject. Notably, the estrogen source may be either exogenous or endogenous. One example of such a method involves coadministering an effective amount of a phytoestrogen compound with an effective amount of an indole compound. In accordance with the present invention, it is thought that the combination of the two compounds provides a synergistic effect on the production of the inactive estrogen metabolite 2-hydroxyestrone, as compared to production of this metabolite by administration of either a phytoestrogen or an indole compound alone.

The specific indole compound utilized can be a number of compounds found in the indole group, for example, indole-3-carbinol, indoleacetic acid, indolebutyric acid, indolmycin, 3-indolylacetone, indomethacin, and indoramin. In one embodiment of the present invention the indole compound selected can be indole-3-carbinol also known as indole-3-methanol. Indole-3-carbinol is a naturally occurring compound and can be derived from a variety of cruciferous plants, such as, broccoli, cabbage, turnips, and brussel sprouts.

As will be recognized by those of ordinary skill in the art, phytoestrogens are abundant in nature and can be derived or extracted from many different species of plants. Specific examples of phytoestrogen compounds that can be utilized in the present invention include without limitation, genistein, diadzein, and equol. In one embodiment the phytoestrogen compound selected can be genistein.

In yet another aspect, the present invention includes a method of synergistically biasing estrogen metabolism in a subject toward the production of 2-hydroxyestrone. Such a method includes administering to a subject an effective amount of an indole compound and an effective amount of a phytoestrogen compound.

In addition to the methods recited herein, the present invention also provides an estrogen metabolite controlling composition having synergistic amounts of an indole compound and a phytoestrogen compound. The indole compound in combination with a phytoestrogen compound can effect estrogen metabolism by shifting the production of 16-alphahydroxyestrone to a more favorable production of 2-hydroxyestrone. Coadministering a phytoestrogen compound with the indole compound is thought to result in additional biasing of estrogen metabolism and result in the production of an unexpected amount of 2-hydroxyestrone metabolite that is synergistic in nature. In one aspect, the increased 2-hydroxyestrone production may yield a 2-hydroxyestrone to 16-hydroxyestrone ratio of from about 1:1 to about 50:1. In another embodiment the ratio may be about 3:1. In a further aspect, the ratio may be from about 2:1 to about 10:1. In yet another aspect, the ration may be from about 5:1 to about 20:1.

The type and amounts of indole and phytoestrogen ingredients contained in a formulation may vary somewhat in order to provide a formulation with specifically desired characteristics. As noted above, a wide variety of specific phytoestrogens and indole compounds may be used. However, in one aspect of the present invention the effective amounts of phytoestrogen utilized may be at least about 1.0 w/w %. In another aspect of the present invention the phytoestrogen amount may be from about 0.25 w/w % to about 20 w/w %. In yet another aspect of the present invention the effective amount of the indole compound may be about 9.0 w/w %. In still another aspect of the present invention the effective amount of indole can be from about 1.0 w/w % to about 50 w/w % of the composition. Further, the ratio of the effective amount of the indole compound to the phytoestrogen compound can be from about 1:1 to 12:1.

In addition to the above-recited indole and phytoestrogen ingredients, lignans can be further used in the methods and the compositions of the present invention to enhancer or improve the synergistic effect obtained. Lignans can be derived or extracted from flax seeds to obtain a lignan precursor which can be converted in the stomach to phytoestrogen lignans. Supplementing the diet with flax seed has shown to alter metabolism of estrogen in a subject. Thus, the addition of a lignan to the composition in the present invention can aid in the synergic effects of controlling an estrogen metabolite.

In another aspect, the composition of the present invention may include one or more traditional estrogens, such as conjugates estrogens, estradiol, etc. A more detailed list of traditional estrogens that can be included in the present composition may be found in U.S. Pat. No. 6,583,129, which is incorporated herein by reference. The amount of estrogen included in the formulation may vary by the specific activity of the estrogen compound used. However, those of ordinary skill in the art will be able to readily ascertain a suitable dosage amount of estrogen for a given purpose (i.e. hormone replacement therapy, supplementation, or contraception) through monitoring a subject to which the composition is administered.

In yet another aspect of the present invention, a variety of other beneficial positive health imparting active agents may be included in the formulation of the present invention in order to produce a desired result or effect. Examples of such agents include without limitation, vitamins, minerals, herbal and plant extracts, enzymes, and amino acids.

In still another aspect of the present invention, the active agents may be combined with at least one excipient and/or at least one carrier. In order to produce a specifically desired dosage formulation. A variety of excipient and carrier materials are known to those of ordinary skill in the art, as well as the type and amount required to provide various dosage forms.

In one aspect of the present invention, the composition may be provided as an oral dosage form. A variety of oral dosage forms are well known to those of ordinary skill in the art, and specific formulation ingredients may be selected in order to provide a specific result. Examples of oral dosage forms include without limitation, oral dosage forms, such as powders, tablets, capsules, gel capsules, liquids, syrups, elixirs, and suspensions. Additionally, oral dosage forms encompass food preparations, such as bars and beverages. Accordingly, in one aspect of the present invention, the composition may be a dosage form selected from the group consisting of beverages, effervescent beverages, liquids, syrups, elixirs, suspensions, tablets, powders, capsules, gel capsules, confections, candies, bars, lozenges, and combinations thereof. In a further aspect of the present invention the beverage dosage form may utilize a powder form of the composition of the present invention, where the beverage formulation utilizes other ingredients, such as sweeteners, colorants and effervescent causing ingredients. In yet a further aspect of the present invention, the composition may be administered by means of a transdermal matrix, liquid reservoir patches, or topical formulations, such as gels, creams, lotions, ointments and nasal sprays.

In another aspect, the formulation can be included in an effervescent tablet or powder. In such cases, the compound can be delivered to a subject by dissolving the effervescent tablet in a liquid for subsequent ingestion. The effervescent formulation may contain a carbonate salt, such as sodium bicarbonate, and an acidic material, such citric acid. When dispensed in water, these components react to create effervescence. Additionally, the formulation may include a lubricant, such a polyethylene glycol, and a binding agent, or binder, which is preferably polyvinylpyrrolidone. The effervescent formulation may also include a flavor agent, and may optionally contain a sweetening agent such as sugar, aspartame, saccharin, or any other natural sweetener.

As discussed above, the present invention additionally encompasses methods for providing estrogen supplementation to a subject disclosed herein. In one aspect, the present invention provides a method for improving the in-vivo performance of phytoestrogens, which includes coadministering a therapeutic effective amount of indole-3-carbinol with the phytoestrogen to a subject. In yet another aspect, the present invention provides a method for treating, ameliorating, or preventing symptoms associated with estrogen deficiency or imbalance in a subject, which also includes administering an effective amount of indole-3-carbinol and phytoestrogen to the subject. Such extracts may be provided as part of any of the formulations disclosed herein, or may simply be administered directly to the subject. Further, such ingredients may be administered as a single composition, or as different compositions.

In accordance with the above described compositions and methods of use thereof, the composition can be administered on a daily basis as needed or according to a specific and customized dosing regimen. Accordingly, administering the composition can include a single daily dose, and can further include multiple doses per day.

The following examples will enable those skilled in the art to more clearly understand how to practice the present invention. It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES

Example 1

In one embodiment, soft gel capsules may be used as a formulation for use in the present invention. Table 1 illustrates one embodiment of a soft gel formulation.

TABLE 1

| Ingredients | Dosage (mg/day) |
| --- | --- |
| Borage Seed Oil, 17-25% GLA | 250 |
| Evening Primrose Oil 8-14% GLA | 500 |
| Indole-3-carbinol | 100 |
| Chasteberry PE 0.5% | 250 |
| Pomegranate extract | 40 |
| Lignans from Flaxseed (Linulife) | 15 |
| Genistein from soy isoflavones | 10 |

As a general matter, soft gel capsules are prepared by mixing glycerin, gelatin, carob and polysorbate together with water in a gelatin melter. Color is also added in the mixing stage. The melted gelatin mixture is placed in an encapsulation unit. The melted gelatin mixture solidifies to obtain a gelatin ribbon. The gelatin ribbon is filled and sealed with the formulation inside. The filled gelatin ribbon is cut and formed into soft gelatin capsules. Finally, the soft gelatin capsules are tumbled dried.

Example 2

Dry powder formulations in accordance with two embodiments of the present invention are prepared to include ingredients and amounts as recited in Tables 2 & 3.

TABLE 2

| Ingredients | Dosage (mg/day) |
| --- | --- |
| Black Cohosh Extract (2.5% triterpenes) | 40 |
| Pomegranate Extract | 40 |
| Lignans from Flaxseed (Linulife) | 20 |
| Genistein from soy isoflavones | 15 |
| Indole-3-carbinol | 100 |
| Broccoli Powder | 200 |

TABLE 3

| Ingredients | Dosage (mg/day) |
| --- | --- |
| Indole-3-carbinol | 100 |
| Genistein from soy isoflavones | 45 |
| Lignans from Flaxseed (Linulife) | 20 |
| Pomegranate Extract | 40 |
| Broccoli Powder | 200 |

Generally, a dry powder formulation is prepared by placing the specified amounts of each ingredient in a V-Blender. The ingredients are mixed and pulverized until a granular mixture is obtained. The dry powder formulation can then be formed in several specific processes for producing various typical oral dosage forms as known by those of ordinary skill in the art. The powdered forms may then be either compressed into tablets and coated, or filled into gelatin capsules and sealed. Other forms, such as those enumerated above may also be produced by further processing the powdered formulation.

What is claimed is:

1. An estrogen metabolite controlling composition comprising:
    a lignin from flax seeds;
    a pharmaceutically acceptable carrier; and
    an amount of an indole compound and a phytoestrogen compound, said compounds present in amounts which together are sufficient to affect the estrogen metabolism by shifting production of a 16-alphahydroxyestrone metabolite to a 2-hydroxyestrone metabolite, wherein the composition is an oral dosage form selected from the group consisting of a powder, a tablet, an effervescent tablet, a capsule, a gel capsule, a confection, a candy, a bar, and a lozenge.

2. The composition of claim 1, wherein the indole compound is a member selected from the group consisting of: indole-3-carbinol, indoleacetic acid, indolebutyric acid, indolmycin, 3-indolylacetone, indomethacin, and indoramin.

3. The composition of claim 2, wherein the indole compound is indole-3-carbinol.

4. The composition of claim 1, wherein the phytoestrogen is a plant derived compound having a diphenolic structure resembling the structure of a synthetic estrogen.

5. The composition of claim 4, wherein the phytoestrogen is an isoflavone.

6. The composition of claim 5, wherein the isoflavone is a member selected from the group consisting of: genistein, diadzein, equol.

7. The composition of claim 6, wherein the isoflavone is genistein.

8. The composition of claim 4, wherein the phytoestrogen is a glycoside.

9. The composition of claim 1, wherein the phytoestrogen is genistein, and the indole compound is indole-3-carbinol.

10. The composition of claim 1, wherein the indole compound in the composition is derived from a plant source and the plant source comprises a member selected from the group consisting of: broccoli, cabbage, turnips, brussel sprouts, or a combination thereof.

11. The composition of claim 1, wherein the shifting production yields a 2-hydroxyestrone to 16-hydroxyestrone ratio of about 5:1 to about 20:1.

12. The composition of claim 1, wherein an effective amount of the indole compound in the composition comprises from about 1.0 w/w % to about 50 w/w % of the composition.

13. The composition of claim 1, wherein an effective amount of the phytoestrogen compound in the composition comprises from about 0.25 w/w % to about 20 w/w % of the composition.

14. The composition of claim 1, wherein a ratio of an effective amount of the indole compound to the phytoestrogen compound can be from about 1:1 to about 12:1.

15. The composition of claim 1, wherein the indole compound in a dose of the composition comprises about 100 mg per day.

16. The composition of claim 1, wherein the phytoestrogen compound in a dose of the composition comprises from about 10 mg per day to about 45 mg per day.

17. The composition of claim 1, further comprising a member selected from the group consisting of: estrogens, vitamins, minerals, herbal and plant extracts, enzymes, amino acids, and combinations thereof.

* * * * *